(12) United States Patent
Lee

(10) Patent No.: US 6,232,113 B1
(45) Date of Patent: May 15, 2001

(54) PARTICLE BOMBARDMENT DEVICE

(76) Inventor: Tien-Li Lee, 8078 Regents Rd. #101, San Diego, CA (US) 92122

( * ) Notice: Subject to any disclaimer, the term of this patent is extended or adjusted under 35 U.S.C. 154(b) by 0 days.

(21) Appl. No.: 09/455,961

(22) Filed: Dec. 6, 1999

Related U.S. Application Data

(60) Provisional application No. 60/111,373, filed on Dec. 8, 1998.

(51) Int. Cl.⁷ .................................... C12M 3/00
(52) U.S. Cl. ................... 435/285.3; 435/459; 604/60; 604/70; 604/140
(58) Field of Search ............... 435/285.1, 285.3, 435/459; 604/60, 61, 70, 73, 130, 140; 124/83

(56) References Cited

U.S. PATENT DOCUMENTS

| | | | |
|---|---|---|---|
| 4,945,050 | 7/1990 | Sanford | 435/172.1 |
| 5,066,587 | * 11/1991 | Jones et al. | 435/285.3 |
| 5,240,855 | 8/1993 | Tomes | 435/287 |
| 5,405,779 | 4/1995 | McCabe | 435/287 |
| 5,506,125 | 4/1996 | McCabe | 435/172.1 |
| 5,525,510 | 6/1996 | McCabe | 435/285.3 |
| 5,584,807 | 12/1996 | McCabe | 604/71 |
| 5,701,878 | * 12/1997 | Moore et al. | 124/83 |
| 5,733,600 | 3/1998 | McCabe | 427/183 |
| 5,753,496 | * 5/1998 | Morikawa et al. | 435/285.3 |

* cited by examiner

Primary Examiner—William H. Beisner

(57) ABSTRACT

An improved particle bombardment device for transporting biological substances such as DNA into living cells. The device has a flexible barrel (40) that facilitates endoscopic particle bombardment of in vivo cells without a significant concomitant blast effect and without a need for a vacuum. The device also involves a unique tapered particle-carrying macroprojectile that can travel through convolutions of such a flexible barrel (40) with minimal friction.

8 Claims, 3 Drawing Sheets

PARTICLE BOMBARDMENT DEVICE

CROSS-REFERENCES TO RELATED APPLICATIONS

Figure 1:
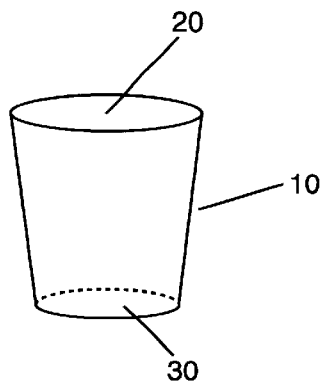

This application claims the benefit of Provisional Patent Application Serial# 60/111,373, filed Dec. 8, 1998.

BACKGROUND

1. Field of Invention

This invention relates to field of delivering genetic material into cells, specifically to an improved particle bombardment apparatus for delivering genetic material into living cells.

2. Discussion of Prior Art

Particle-mediated delivery of genetic material into living cells has become a powerful tool for medical research and biotechnology. Existing particle bombardment devices propel inert or biologically active particles at speeds great enough to penetrate the surface of cells. These particles are typically used as carriers to deliver genetic material or transgenes into target cells in vivo or in vitro. The transgenes may then integrate into the germ line of plant and animal cells.

Judging from recent advances in gene therapy research, many diseases may eventually be treated by the transformation of patient cells with appropriate transgenes. However, existing particle bombardment systems are inadequate for delivering high-speed particles to fragile in vivo cells such as, but not limited to, those found in lung or embryonic tissue. Firstly, many current devices use mechanisms of particle delivery that are harmful to fragile cells. Most cells can recover from the penetration of the actual particles, but collateral damage from secondary blast effects destroys some types of cells. Secondly, there is presently no endoscopic particle bombardment device capable of delivering particles at a high speed through a flexible or convoluted passageway of varying shape or dimension. Therefore, many human cells in vivo are currently physically inaccessible for particle bombardment gene therapy.

Many apparatuses and methods have been used to accelerate particles into cells, but often, many damage target cells in the process. For example, in one method disclosed by U.S. Pat. No. 4,945,050 to Sanford (1990), particles are entrained in a pressurized stream of gas through a barrel and are thereby accelerated to the target. However, the use of gas pressures sufficient to accelerate particles enough to penetrate cells often result in damage to fragile cells via a blast effect from the gas itself. Most plant cells, and certain animal cells can withstand the blast, but many types of cells cannot. As an attempt to address this issue, U.S. Pat. No. 5,525,510 (1995) to Dennis McCabe discloses an exit nozzle with a conical taper used to disperse the blast effect. While this design does slightly reduce the effect of the blast, it still does not prevent damage to certain types of animal cells.

In another method disclosed by U.S. Pat. No. 4,945,050 to Sanford (1990), a macroprojectile or bullet is used to accelerate particles. An explosive charge accelerates the bullet along with particles in a forward chamber through a barrel. At the exit port, a stop plate with an aperture stops the bullet but allows the particles to continue toward the target. There are exhaust vents present near the muzzle to divert compressed gas ahead of the bullet so as to reduce blast effects. Nevertheless, this design also cannot be used for endoscopic applications since the cylindrical nature of the bullet does not allow the delivery of particles through a convoluted or flexible barrel or corridor of varying shape.

In another popular method disclosed by U.S. Pat. No. 5,506,125 to Dennis McCabe (1996), particles are accelerated on a carrier sheet. A retaining screen stops the carrier sheet but allows the particles to continue on their course toward the cells. The blast effect from this method is, in general, less pronounced; but since aerodynamic drag significantly slows the particles in the space between the retaining screen and the target, partial evacuation of the test chamber is necessary. However, cell viability is reduced at pressures less than 200 millibars. Additionally, evacuation is not even feasible if the target cells are internal in vivo cells from a human patient. Furthermore, the use of a carrier plate makes this method impossible to apply to an endoscopic system where the plate would need to travel though a convoluted or flexible corridor of varying shape.

OBJECTS AND ADVANTAGES

Several objects and advantages of the present invention are a) To provide a means to propel inert or biologically active particles at speeds great enough to penetrate the surface of cells through a convoluted and flexible barrel which can be used for endoscopic applications.

b) To provide a means to propel inert or biologically active particles at speeds great enough to penetrate the surface of cells without causing a significant concomitant blast effect from gas.

c) To provide a means to propel inert or biologically active particles at speeds great enough to penetrate the surface of cells without the need for evacuation of the target area.

DRAWING FIGURES

Figure 2:
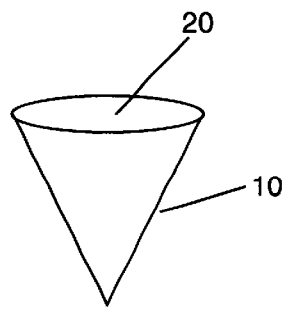
Figure 3:
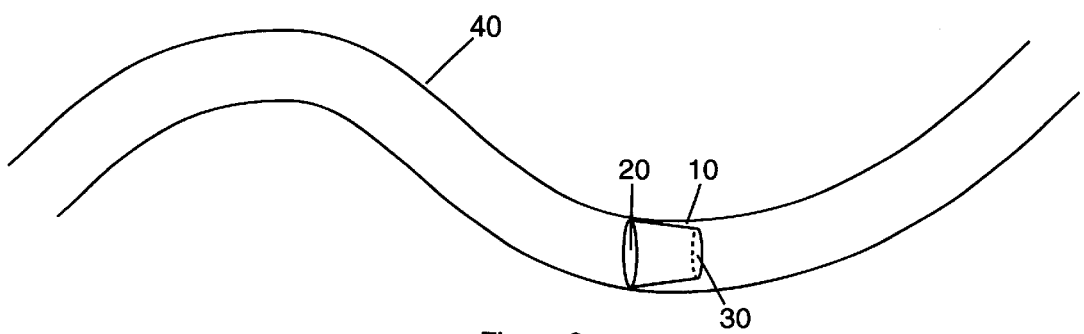
Figure 4:
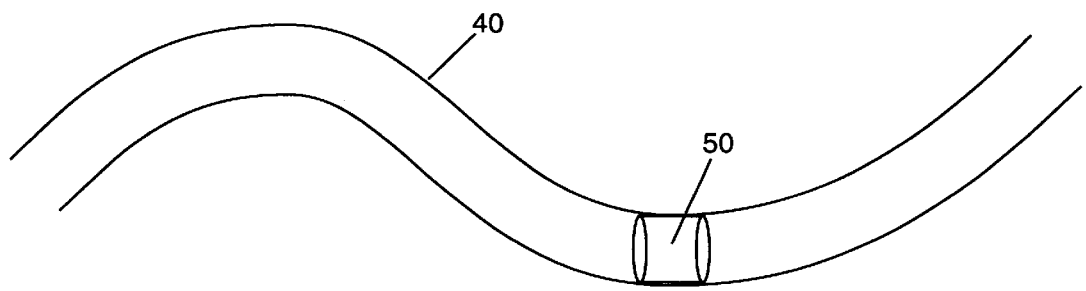
Figure 5:
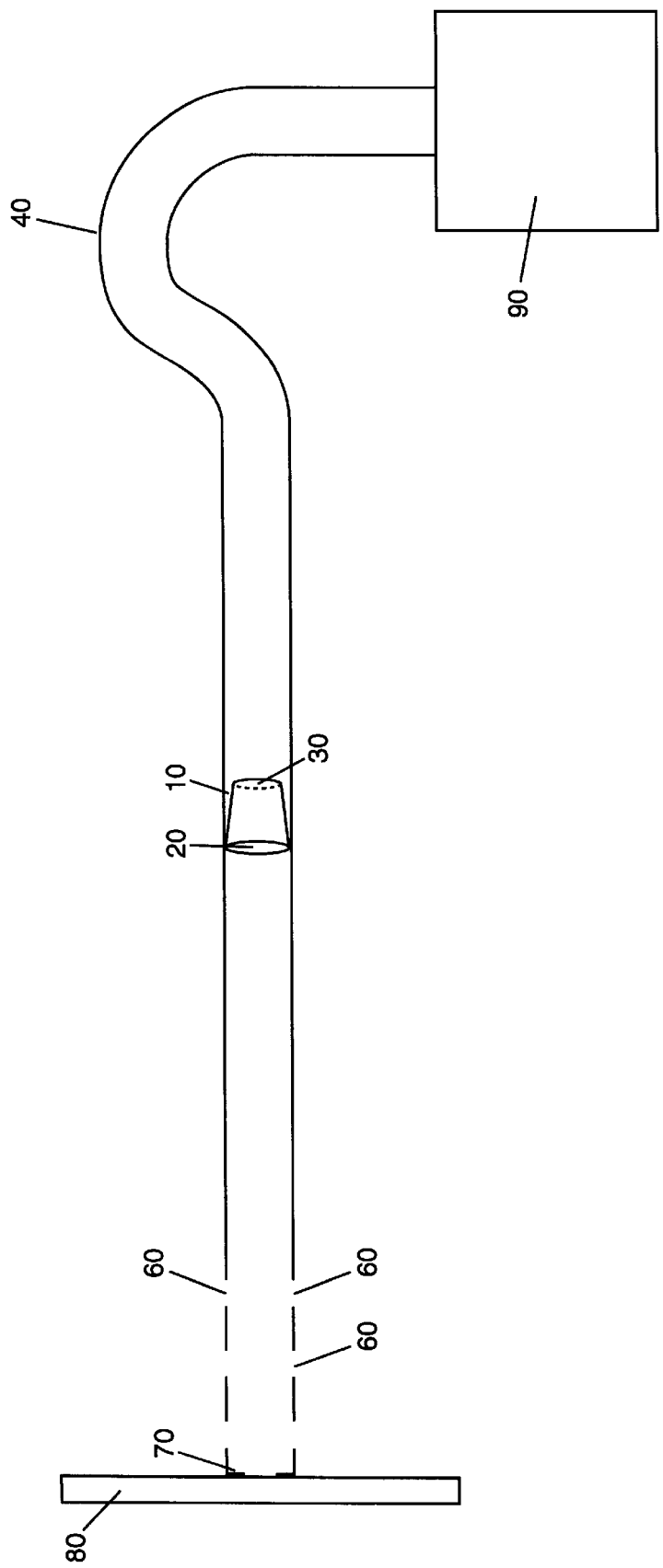
Figure 6A:
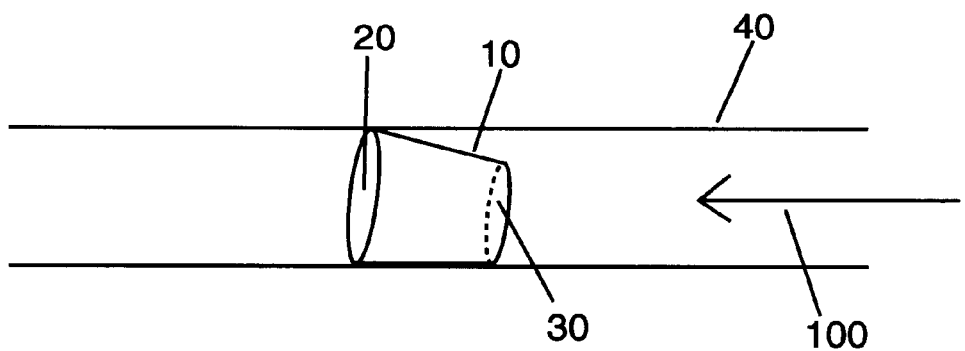
Figure 6B:
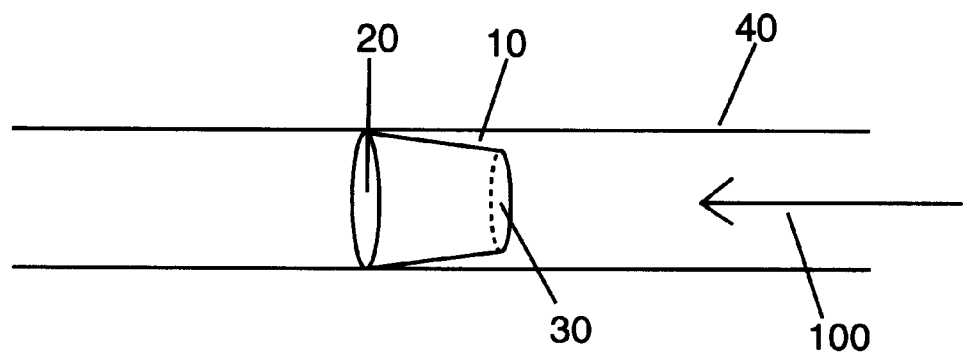

In the drawings, closely related figures have the same number but different alphabetic suffixes FIG. 1 shows a macroprojectile particle carrier with both ends closed FIG. 2 shows a conical macroprojectile carrier with a closed end or base FIG. 3 shows a macroprojectile traversing a flexible and convoluted barrel FIG. 4 shows a cylindrical macroprojectile failing to traverse a flexible and convoluted barrel FIG. 5 shows a flexible barrel with multiple vents and a stop mechanism FIG. 6A shows a macroprojectile not oriented parallel to the axis of a barrel FIG. 6B shows a macroprojectile oriented parallel to the axis of a barrel

| Reference Numerals in Drawings | |
|---|---|
| 10 body of macroprojectile | 20 particle-carrying base of macroprojectile |
| 30 proximal base of macroprojectile | 40 barrel |
| 50 cylindrical macroprojectile | 60 exhaust vent |
| 70 stop mechanism | 80 target surface |
| 90 propellant source | 100 force vector |

SUMMARY

In accordance with the present invention, a macroprojectile particle carrier comprises a tapered body with one end having a cross-sectional area approximately equal to that of the barrel and one end having a cross-sectional area less than that of the barrel. Additionally, a barrel comprises a hollow body with uniform internal cross-sectional area, one or multiple exhaust vents, and a stop mechanism. The physical characteristics of this macroprojectile will allow it to be accelerated through the described flexible barrel with minimal frictional forces and deliver particles to a distal target with minimal blast effects.

Description

A typical embodiment of the macroprojectile of the present invention is illustrated in FIG. 1. The macroprojectile has a tapered body 10 made of a durable material. The particle-carrying base 20 possesses a cross-sectional area approximately equal to the barrel that transmits the macroprojectile. Particle-carrying base 20 will also be capable of carrying inert or biologically active particles on its surface. A proximal base 30 will have a cross-sectional area less than the barrel that transmits the macroprojectile.

FIG. 2 shows an additional embodiment of the macroprojectile. In FIG. 2, there is no proximal base. There are various possibilities with regard to the specific shape of the macroprojectile. The body 10 does not have to be conical in nature; nor does the particle-carrying base 20 have to circular in nature. The only requirements are that the particle-carrying base 20 approximates the cross-sectional shape and area of the barrel that transmits the macroprojectile, and that the body 10 has a generally tapered structure.

FIG. 3 shows a barrel 40 and the macroprojectile described in FIG. 1. The barrel 40 is flexible in nature and can vary in shape but maintains a uniform cross-sectional area at points along its length. In the preferred embodiment, the barrel is made of or lined with a material that reduces fiction with the macroprojectile. This material can be, for example, a fluoropolymer-containing substance.

FIG. 4 shows a cylindrical macroprojectile 50 in a barrel 40. It is graphically illustrated here that a cylindrical macroprojectile with any given cross-sectional area cannot easily traverse a convoluted passageway of the same cross-sectional area.

A typical embodiment of the present invention is illustrated in FIG. 5. There is the barrel 40, the macroprojectile from described in FIG. 1, an exhaust vent 60, a stop mechanism 70, a target surface 80, and a propellant source 90. The exhaust vent 60 may be any perforation of the solid structure of the barrel 40 which would allow gases pushed ahead of the macroprojectile to escape. This reduces the blast effect of gas from damaging any cells in the target surface 80. Due to these vents, the barrel 40 can therefore be placed directly on the target surface 80 without causing a damaging blast effect. As an optional feature, a pump may be connected to the exhaust vents to facilitate the movement of compressed gas out of the barrel 40. A stop mechanism 70 retains the macroprojectile within the barrel but permits the particles to continue travelling toward the target. The stop mechanism can be an O-ring, a net-like mesh, or any other object capable of retaining the macroprojectile within the barrel 40 and permitting the passage of smaller particles. A propellant source 90 is necessary to drive the macroprojectile along the barrel 40 towards the target surface 80 at a speed great enough to cause the particles placed on particle-carrying base 20 to penetrate cells on the target surface 80. The propellant source 90 may be any source of potential mechanical energy regulated by a trigger mechanism (not shown). For example, the propellant source 90 can be a reservoir of compressed gas regulated by a valve. In another example, propellant source 90 can accelerate the macroprojectile through an electromagnetic means.

FIG. 6A demonstrates the macroprojectile of FIG. 1 traversing the barrel 40. The axis of the macroprojectile is not parallel to the barrel 40. A force vector 100 is applied to the macroprojectile due to activation of a propellant source. FIG. 6B shows the same macroprojectile with its axis parallel to barrel 40 with a force vector 100 applied to it. These two figures graphically illustrate how the geometric shape of the macroprojectile of FIG. 1 allows it to keep its axis approximately parallel to the barrel 40. This is because it system is most energetically favorable when the macroprojectile has its axis parallel to the barrel 40.

From the descriptions above, a number of advantages of this macroprojectile and barrel design become evident:

a) This flexible barrel 40 may be used to access in vivo human cells in the interior of a patient.

b) The unique shape of the macroprojectile from FIG. 1 or FIG. 2 allows its movement through a convoluted passageway with minimal frictional forces.

c) Singular or multiple vents 60 in a barrel reduce effects of damaging gas blasts to cells.

d) The placement of the distal end of the barrel 40 directly on the target surface 80 minimizes the distance the particles must travel from particle-carrying base 20 to the target surface 80. Therefore, a vacuum is not necessary for particle impact speed to be sufficient to penetrate target cells.

Operation

The manner of using this system is similar to that for a bullet macroprojectile particle accelerator described in U.S. Pat. No. 4,945,050 to Sanford (1990).

DNA or biologically active matter is adhered to carrier particles such as, but not limited to, gold granules. These carrier particles are then in turn adhered to the particle-carrying base 20 of the macroprojectile in FIG. 1 or FIG. 2. The macroprojectile is then loaded into the barrel 40 near the propellant source 90. The distal end of barrel 40 is then maneuvered and placed on the target surface 80. A trigger mechanism will then be activated which will release a propellant from propellant source 90. The macroprojectile will then be accelerated distally along the flexible barrel 40. The geometry of the macroprojectile will minimize functional forces and maintain its axis approximately parallel to the barrel 40. The gas or air pushed in front of the travelling macroprojectile will be diverted outwards from the barrel 40 through one or multiple exhaust vents 60. The macroprojectile will contact a stop mechanism 70 that will retain the macroprojectile within the barrel 40 but permit the passage of particles out of the barrel 40. The particles will then impact and penetrate cells in the target surface 80.

Conclusion, Ramification, and Scope

The reader will see that the macroprojectile and flexible barrel design described above will permit the safe, convenient, and effective application of endoscopic particle bombardment.

While the above description contains many specificities, these should not be construed as limitations on the scope of the invention, but rather as an exemplification of one preferred embodiment thereof. For example, the macroprojectile may be accelerated through the barrel by some other means besides a gaseous propellant. An electromagnetic means could be employed to accelerate the macroprojectile for instance. Additionally, the exhaust vents could be replaced with vacuums or pumps that actively remove air or gas.

Accordingly, the scope of the invention should be determined not by the embodiments illustrated, but by the appended claims and their legal requirements.

I claim:

1. An improved particle bombardment device for transporting genetic material into living cells, comprising:
   a) a flexible barrel of a predetermined cross-sectional area and shape
   b) a tapered particle-carrying macroprojectile with a maximum distal cross-sectional area and shape approximately equal to the cross-sectional area and shape of said barrel
   c) an accelerating means for propelling said macroprojectile through said barrel
   d) a variable number of exhaust vent perforations in the structure of the distal end of said barrel which allow for the escape of pressurized gas from said barrel
   e) a stop mechanism at the distal end of the barrel that provides a means for retaining said macroprojectile and permitting the exit of smaller particles initially carried on said macroprojectile.

whereby particles carrying genetic material may be delivered into in vivo cells through an endoscopic device without a significant damaging blast effect.

2. The particle bombardment device of claim 1 wherein the barrel is lined in its interior with a low-friction substance.

3. The particle bombardment device of claim 2 wherein the low-friction substance is a fluoropolymer.

4. The particle bombardment device of claim 1 wherein the accelerating means for propelling said macroprojectile is compressed gas released via a trigger mechanism.

5. The particle bombardment device of claim 1 wherein the accelerating means for propelling said macroprojectile is an electromagnet.

6. The particle bombardment device of claim 1 wherein the stop mechanism is a ring placed at the distal end of said barrel.

7. The particle bombardment device of claim 1 wherein the stop mechanism is a net-like structure.

8. The particle bombardment device of claim 1 further including a pump apparatus that removes pressurized gas from said barrel through said exhaust vent perforations.

* * * * *